United States Patent [19]

Metcalf et al.

[11] Patent Number: 5,453,094
[45] Date of Patent: Sep. 26, 1995

[54] KIT ASSEMBLY FOR USE DURING A LAPAROSCOPIC SURGICAL PROCEDURE

[75] Inventors: Gerald L. Metcalf, Burnsville; Vern E. Radewald, Maplewood; Melinda K. Samples, Roseville; Kraig M. Keister, Bloomington; George L. Sommerfeld, Shoreview; Alan J. Solyntjes, Richfield, all of Minn.

[73] Assignee: Minnesota Mining and Manufacturing Company, St. Paul, Minn.

[21] Appl. No.: 123,351

[22] Filed: Sep. 17, 1993

[51] Int. Cl.$^6$ .................................................. A61M 5/00
[52] U.S. Cl. .................... 604/164; 604/264; 206/366; 206/571
[58] Field of Search .................................. 604/164, 264; 206/366, 571

[56] References Cited

U.S. PATENT DOCUMENTS

| | | | |
|---|---|---|---|
| 3,817,251 | 6/1974 | Hasson | 128/348 |
| 4,106,620 | 8/1978 | Brimmer et al. | |
| 4,253,830 | 3/1981 | Kazen et al. | 433/77 |
| 4,319,575 | 3/1982 | Bonte | |
| 4,535,773 | 8/1985 | Yoon | 604/51 |
| 4,601,710 | 7/1986 | Moll | 604/165 |
| 4,617,933 | 10/1986 | Hasson | 128/348.1 |
| 4,654,030 | 3/1987 | Moll et al. | 604/165 |
| 4,872,451 | 10/1989 | Moore et al. | 128/92 YF |
| 4,902,280 | 2/1990 | Lander | 604/165 |
| 4,903,390 | 2/1990 | Vidal et al. | 29/239 |
| 4,909,789 | 3/1990 | Taguchi et al. | 604/107 |
| 4,931,042 | 6/1990 | Holmes et al. | 604/164 |
| 4,943,280 | 7/1990 | Lander | 604/169 |
| 4,976,616 | 12/1990 | Eisner et al. | 433/77 |
| 5,030,206 | 7/1991 | Lander | 604/164 |
| 5,057,082 | 10/1991 | Burchette, Jr. | 604/164 |
| 5,066,288 | 11/1991 | Deniega et al. | 604/274 |
| 5,071,346 | 12/1991 | Domaas | 433/77 |
| 5,104,382 | 4/1992 | Brinkerhoff et al. | 604/165 |
| 5,108,287 | 4/1992 | Yee et al. | 433/77 |
| 5,116,353 | 5/1992 | Green | 606/184 |
| 5,122,122 | 6/1992 | Allgood | 604/174 |
| 5,127,909 | 7/1992 | Shichman | 604/165 |
| 5,129,885 | 7/1992 | Green et al. | 604/164 |
| 5,135,525 | 8/1992 | Biscoping et al. | 604/51 |
| 5,144,942 | 9/1992 | Decarie et al. | 128/4 |
| 5,152,754 | 10/1992 | Plyley et al. | 604/164 |
| 5,158,552 | 10/1992 | Borgia et al. | 604/165 |
| 5,176,651 | 1/1993 | Allgood et al. | 604/167 |
| 5,217,451 | 6/1993 | Freitas | 606/1 |
| 5,224,930 | 7/1993 | Spaeth et al. | 604/33 |
| 5,224,951 | 7/1993 | Freitas | 606/172 |

(List continued on next page.)

FOREIGN PATENT DOCUMENTS

| | | |
|---|---|---|
| 0312219 | 4/1989 | European Pat. Off. . |
| 0520296 | 12/1992 | European Pat. Off. . |
| 0546769 | 6/1993 | European Pat. Off. . |
| 0578102 | 1/1994 | European Pat. Off. . |
| 0595090 | 5/1994 | European Pat. Off. . |
| 9100457 | 5/1991 | Germany . |
| 921554 | 3/1963 | United Kingdom . |
| 2103936A | 2/1983 | United Kingdom . |
| WO93/04716 | 3/1993 | WIPO . |
| WO93/04715 | 3/1993 | WIPO . |
| WO93/04632 | 3/1993 | WIPO . |

OTHER PUBLICATIONS

Product brochure for "Gemini™ Disposable/Reusable Trocare Cannula System", by Minorax Corporation (2 pages).
United States Surgical Corporation, 1992 Annual Report, pp. 20–23.

*Primary Examiner*—John G. Weiss
*Attorney, Agent, or Firm*—Gary L. Griswold; Walter N. Kirn; Jeffrey J. Hohenshell

[57] ABSTRACT

A kit assembly for use during a laparoscopic surgical procedure. The kit assembly may have a plurality of cannula or a plurality of trocar assemblies. The kit assembly affords the convenient use of different types of trocar or cannula assemblies during a laparoscopic surgical procedure.

10 Claims, 3 Drawing Sheets

U.S. PATENT DOCUMENTS

| | | | |
|---|---|---|---|
| 5,224,954 | 7/1993 | Watts et al. | 606/205 |
| 5,226,426 | 7/1993 | Yoon | 128/753 |
| 5,232,450 | 8/1993 | Green et al. | 604/164 |
| 5,256,147 | 10/1993 | Vidal et al. | 604/158 |
| 5,290,217 | 3/1994 | Campos | 600/37 |
| 5,300,036 | 5/1994 | Mueller et al. | 604/167 |
| 5,300,070 | 4/1994 | Gentelia et al. | 606/45 |
| 5,300,072 | 5/1994 | Aghion | 606/59 |
| 5,315,985 | 5/1994 | Decarie et al. | 128/4 |

KIT ASSEMBLY FOR USE DURING A LAPAROSCOPIC SURGICAL PROCEDURE

TECHNICAL FIELD

The present invention is directed generally to kit assemblies for use in a laparoscopic surgical procedure, and more particularly to a kit assembly which includes trocars for inserting an access tube or "cannula" through an abdominal wall, and associated access tubes.

BACKGROUND OF THE INVENTION

An increasing number of abdominal surgical procedures are being performed with laparoscopic techniques in order to avoid a large skin incision. Typically in laparoscopic surgery, a special needle, similar to the pneumoneedles described in U.S. Pat. No. 4,808,168 to Warring and U.S. patent application Ser. No. 07/808,152 (both of which are herein expressly incorporated by reference), is inserted through the skin, and used to inflate the abdominal cavity with an insufflating gas such as $CO_2$. Once the abdomen is adequately dilated, the needle is removed and a rigid cannula with an access tube with a larger diameter (for example 5, 10 or 11 mm) is passed through the skin in the same location.

The access tube provides access for laparoscopes or other laparoscopic surgical tools such as the stapler described in U.S. Pat. No. 5,040,715 or the surgical clip appliers described in U.S. Pat. No.'s 5,084,057 and 5,100,420. To drive the access tube through the skin, the surgeon places a trocar obturator in the lumen of the access tube to provide a sharp, leading edge for cutting tissue. Often several trocar and cannula assemblies are used during a laparoscopic surgical procedure on the same patient.

The art is replete with trocar and cannula devices. Diverse designs for trocar and cannula assemblies exist. Trocars may be constructed (1) to include a mechanism for protecting underlying organs from sharp obturator surfaces, (2) to be reusable on multiple patients, or (3) to be disposable to minimize sterilization and sharpness issues present with reusable trocars. Cannulae may be constructed (1) to include several different features to restrict loss of insufflating gas from the abdominal cavity or to afford replenishment of the insufflating gas within the abdominal cavity, (2) to be disposable, (3) to be reusable, or (4) for specialty applications such as extended length for obese patients or with specialized electrical properties for use with laparoscopic instruments. Additionally, as surgeons gain experience with laparoscopic surgical procedures, they are developing preferences for customized surgical devices, including trocar and cannula assemblies.

Further, cost considerations are becoming increasingly important in the determination of which cannula and trocar assemblies are used during a laparoscopic surgical procedure. For example, a trocar assembly having a mechanism for protecting underlying organs from a sharp obturator tip is typically a complex and expensive device relative to a trocar assembly without such a mechanism.

U.S. Pat. No. 5,144,942 discloses an endoscopic or laparoscopic instrumentation kit comprising a plurality of trocar assemblies and cannula assemblies. The trocar assemblies may comprise different sized (e.g. 5 mm and 10 mm diameters) trocars and the cannula assemblies may comprise different sized cannulae (e.g. 5 mm and 10 mm diameters). However, such packages encounter problems when a surgeon would prefer to take advantage of the features of different types of trocars and different types of cannula.

BRIEF DESCRIPTION OF THE INVENTION

According to the present invention there is provided a kit assembly for use during a laparoscopic surgery. The kit assembly comprises a plurality of trocar or a plurality of cannula assemblies. If the kit assembly comprises a plurality of trocar assemblies, at least two of the trocars comprise different types of trocars. If the kit assembly comprises a plurality of cannula assemblies, at least two of the cannula assemblies comprise different types of.

In a first embodiment of the present invention, the kit assembly comprises a first trocar for use with a cannula to insert the cannula into the abdominal cavity of a patient; and a second trocar for use with a cannula to insert the cannula into the abdominal cavity of a patient. The first trocar comprises a different type of trocar than the second trocar. Finally, a package encloses the first and second trocars.

The first and second trocars may comprise a variety of trocars. For example, one of the trocars may comprise a means for protecting underlying organs from sharp obturator surfaces, and the other trocar may be free of a means for protecting underlying organs from sharp cutting surfaces. Other examples of different types of trocars include: (1) a disposable (e.g. single patient use only) trocar which simplifies sterilization procedures, (2) a reusable trocar which offers reduction in waste advantages, and (3) a trocar with a replaceable obturator with the attendant advantages of such a trocar discussed in commonly owned U.S. patent application No. 07/899,751 filed Jun. 17, 1992, now U.S. Pat. No. 5,256,147 to Claude Vidal and Russell J. Redmond, the entire contents of which are herein expressly incorporated by reference.

Another example of a kit assembly according to the present invention comprises a first cannula adapted to be inserted into the abdominal cavity of a patient by use of a trocar, and a second cannula that is of a different type than the first cannula. A package encloses the first and second cannulae.

One type of cannula may have a means for restricting loss of insufflating gas from the abdominal cavity, such as a valve which is known in the art. Another type of cannula may have a means for affording replenishment of the insufflating gas within the abdominal cavity, such as a stopcock valve which is also known in the art. Each of these features add complexity to the cannula with the attendant potential for increased cost. Thus, a cannula that is free of a means for restricting loss of insufflating gas from the abdominal cavity and that is free of a means for affording replenishment of the insufflating gas within the abdominal cavity is also considered to be a different type of cannula according to the present invention.

Other examples of different types of cannulae include a first cannula that includes predetermined electrical properties, such as an electrically insulated access tube, and a second cannula that does not have the predetermined electrical properties. Radiotranslucency is also considered to be a differentiating characteristic that would qualify a radiotranslucent cannula as a different cannula than a non-radiotranslucent cannula according to the present invention.

Other examples of different types of cannula include: (1) a disposable (e.g. single patient use only) cannula which simplifies sterilization procedures, (2) a reusable cannula which offers reduction in waste advantages, and (3) a cannula with an extended length access tube for use with obese patents. Each cannula described in (1)–(3) is considered to be a different type of cannula according to the present invention.

Another aspect of the present invention includes a package which consists of only a single cannula or a single trocar. Individually packaging trocars and cannulae allow surgeons to mix and match the various features of the trocars and obturators, so that the elements used during the laparoscopic surgical procedure are dictated by surgeon preference rather than the limits of the package.

BRIEF DESCRIPTION OF THE DRAWINGS

The present invention will be further described with reference to the accompanying drawing wherein like reference numerals refer to like parts in the several views, and wherein:

FIGS. 2 through 5 are top plan views of different types of packaged trocars according to the present invention, wherein:

FIG. 2 is a top plan view of a disposable trocar;

FIG. 3 is a top plan view of a trocar having a mechanism for protecting underlying organs from sharp obturator surfaces;

FIG. 4 is a top plan view of a reusable trocar;

FIG. 5 is a top plan view of a trocar having a replaceable obturator distal end portion;

FIGS. 6 through 9 are top plan views of different types of packaged cannulae according to the present invention, wherein:

FIG. 6 is a top plan view of a disposable cannula that is free of means for restricting loss of insufflating gas from the abdominal cavity and which is free of a means for affording replenishment of the insufflating gas within the abdominal cavity;

FIG. 7 is a top plan view of a single patient use only cannula having a means for restricting loss of insufflating gas from the abdominal cavity and a means for affording replenishment of the insufflating gas within the abdominal cavity, FIG. 8 is a top plan view of a cannula having an extended length access tube; and FIG. 9 is a top plan view of a reusable cannula.

DETAILED DESCRIPTION OF THE PREFERRED EMBODIMENT

Figure 1:
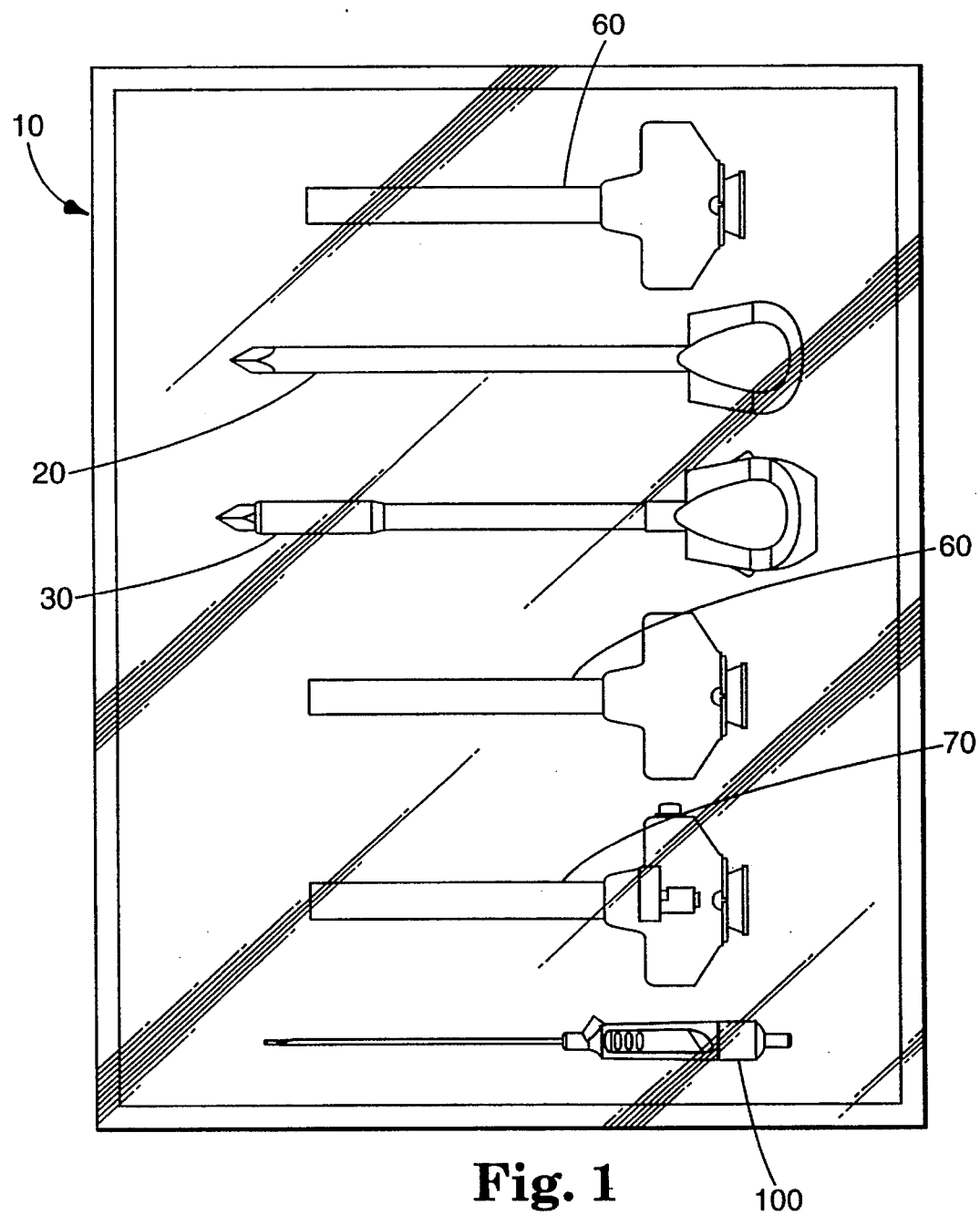
FIG. 1 is a top plan view of one embodiment of a kit assembly for use in a laparoscopic surgical procedure according to the present invention.

Referring now to FIGS. 1 through 9 of the drawing there are shown embodiments of kits or kit assemblies for use during a laparoscopic surgical procedure, one of which is generally designated by reference character 10. The kit assembly 10 comprises either a plurality of trocar assemblies or a plurality of cannula assemblies, or both.

As used herein, the term "trocar" or phrase "trocar assembly" is used generically to describe a variety of devices which include an obturator having a handle portion and a distal portion having surfaces adapted to engage a patient's abdominal wall. Typically, the trocar will have sharp cutting surfaces for piercing the abdominal wall, but it is also contemplated that a trocar may comprise a Hasson-type obturator with a substantially semi-spherical, blunt distal surface.

Trocars within a kit assembly according to the present invention have distal end portions adapted to fit within a lumen of an access tube. Preferably, within a kit assembly according to the present invention, the outer diameter of each of the distal end portions of the trocars are substantially identical.

The term "cannula" or phrase "cannula assembly" is used herein generally to describe a device that includes an access tube having an inner lumen. The trocar obturator is designed to be threaded through the lumen of the access tube. In this condition, the access tube is adapted to be inserted through the abdominal wall and into the abdominal cavity of a patient.

Cannulae according to the present invention include a first cannula having an access tube with a lumen having a first inner diameter, and a second cannula having an access tube with a lumen having a second inner diameter. Preferably, the second inner diameter is substantially the same as the first inner diameter.

If the kit assembly comprises a plurality of trocar assemblies, at least two of the trocars comprise different types of trocars. As used in this application, when it is said that one trocar is of a "different type" than another trocar, it is meant that the trocars substantially differ in features other than size. For example, a trocar for inserting a 5 mm cannula is considered to be the same as a trocar for inserting a 10 mm trocar if this is the only substantial difference between the trocars. Examples of trocars which are considered to be different types of trocars follow with reference to FIGS. 2 through 5.

If the kit assembly comprises a plurality of cannula assemblies, at least two of the cannula assemblies comprise different types of cannulae. As used in this application, when it is said that one cannula is of a "different type" than another cannula, it is meant that the cannulae substantially differ in features other than size. For example, a cannula having an access tube with a 5 mm inner diameter is not considered to different than a cannula having an access tube with a 10 mm inner diameter, if this is the only substantial difference between the cannula. Examples of cannula that are considered to be different types of cannula according to the present invention follow with reference to FIGS. 6 through 9.

Figure 3:
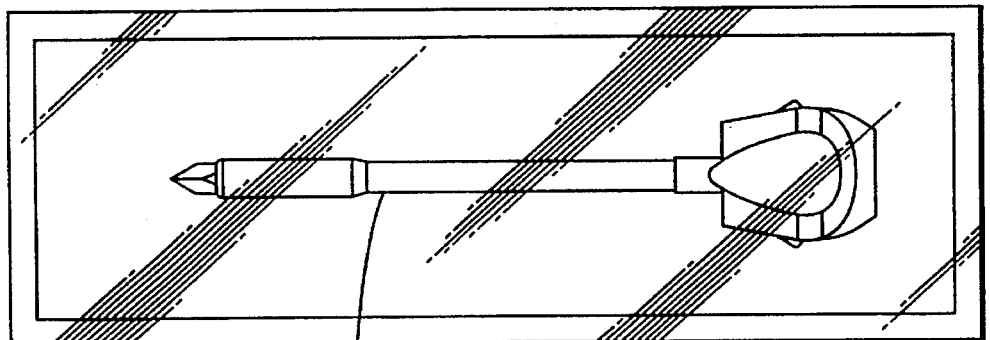

FIG. 3 illustrates a first type of trocar generally designated by reference character 30. The trocar 30 comprises a means for protecting underlying organs from sharp obturator surfaces. As an example only, the trocar 30 may comprise a trocar described in U.S. Pat. No. 5,152,754, the entire contents of which are herein expressly incorporated by reference in its entirety.

Alternatively, a trocar having a means for protecting underlying organs from sharp obturator surfaces may comprise the trocars shown in U.S. Pat. No.'s 4,535,773, 4,601, 710, 4,654,030, 4,902,280, 4,931,042, 5,030,206, 5,066,288, 5,104,382, 5,116,353, 5,158,552, 5,224,951 and 5,226,426, PCT Published Applications No.'s WO 93/04632, WO 93/04715 and WO 93/04716, and Published European Patent Application No. 479,130, the entire contents of each which are herein expressly incorporated by reference. These types of trocar devices are typically used during a surgical procedure on a single patient and then disposed of after the surgical procedure is completed. Two of such trocars currently commercially available are known as the Auto Suture™ Surgiport (generally available from U.S. Surgical of Norwalk, Conn.) and the Endopath™ (generally available from Ethicon of Somerville, N.J.).

Figure 2:
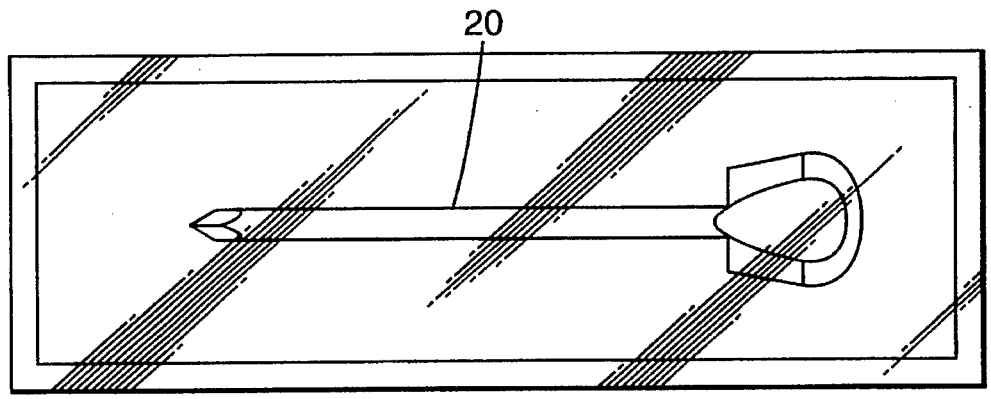

A trocar having a means for protecting underlying organs tends to be expensive and complex to construct. A more cost effective alternative to a trocar having a means for protecting underlying organs from sharp cutting surfaces is shown in FIG. 2 as trocar 20. The trocar 20 has no means for protecting underlying organs from sharp obturator surfaces, but offers significant cost and manufacturing simplification advantages.

Typically, the trocar 20 may be disposed after a laparoscopic procedure on a single patient. Disposing of the trocars after use on a single patient reduces sterilization and maintenance procedures otherwise required of, for example, a reusable trocar and helps to reduce concerns relating to the sharpness of the trocar.

Figure 4:
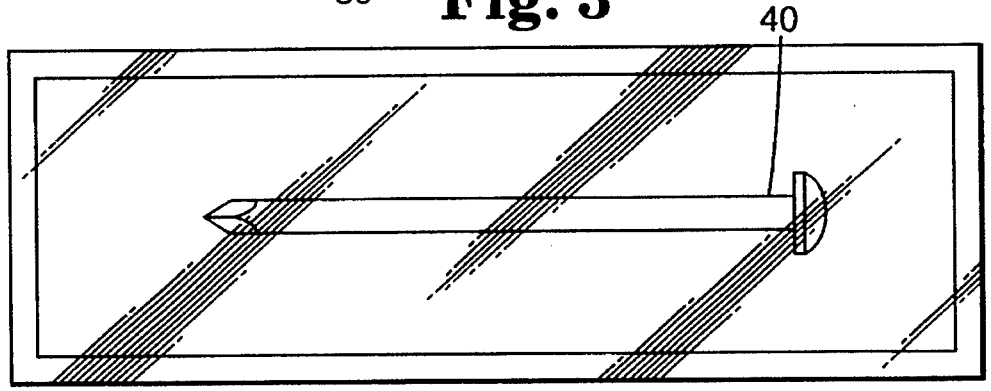

An alternative to the trocar 20 which affords reduction in medical waste advantages is the completely reusable trocar 40 shown in FIG. 4. Commercially available examples of reusable trocars are generally available from Snowden-Pencer, Inc. of Tucker, Ga. and from Solos, Endoscopy, Inc. of Duluth, Ga. As used herein, when it is said that a trocar is reusable, it is meant that the trocar may be used during a surgical procedure, sterilized, and then used again on the same or even a different patient. Reusable trocars tend to have minimal parts to afford quick and convenient cleaning and sterilization of the trocars.

Reusable trocars tend to encounter problems as the sharp tissue cutting surfaces of the obturator (including the tip) tend to become dull after even a few uses. Dulling of the cutting surfaces of the trocar generally tends to increase the insertion force required to insert the trocar into the abdominal cavity.

Figure 5:
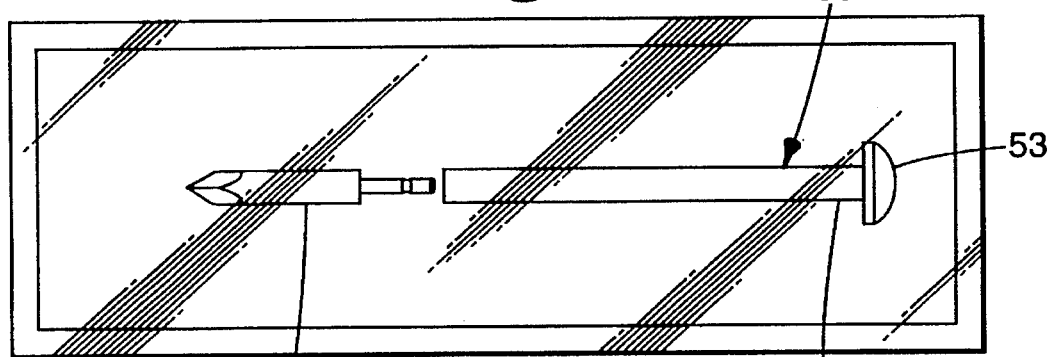

An alternative to a reusable trocar is shown in FIG. 5 as a trocar 50 comprising a proximal portion 51 and a distal end portion 52. The proximal portion 51 comprises a handle 53. The trocar 50 has a detent means for replacing the distal end portion 52 with another distal end portions. The advantages of such a trocar are discussed in commonly owned U.S. patent application No. 07/899,751 filed Jun. 17, 1992 to Claude Vidal and Russell J. Redmond, the entire contents of which are herein expressly incorporated by reference.

Different types of trocars also include a trocar which is specially designed or customized for a particular purpose, or which includes a feature desired by a surgeon for a specialized procedure. Further examples of different types of trocars are shown in published European Patent Application No. 312,219 and U.S. Pat. No. 's 5,057,082, 5,176,651 and 5,224,954, the entire contents of each of which are herein incorporated by reference.

A package encloses the plurality of different types of trocars. The package may comprise a package constructed by any suitable techniques well known in the art. Vacuum forming or thermoforming packages are particular examples. The package should enclose and protect the trocars so that they arrive in the operating room in a sterile condition.

The kit assembly according to the present invention may alternatively be described as a first cannula adapted to be inserted into the abdominal cavity of a patient by use of trocar, and a second cannula that is of a different type than the first cannula. A package encloses the first and second cannulae.

Figure 7:
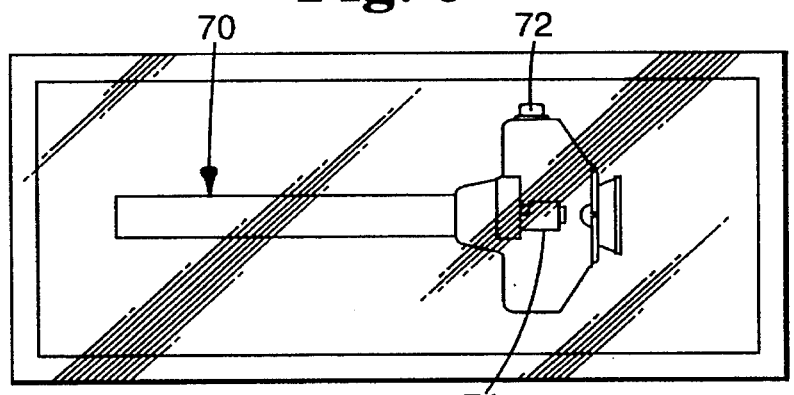

FIG. 7 illustrates a first type of cannula generally designated by reference character 70. The cannula 70 comprises the cannula shown in U.S. Pat. No. 5,152,754 which includes a means for restricting loss of insufflating gas from the abdominal cavity, such as a valve actuated by button 72. The cannula 70 also includes a means for affording replenishment of the insufflating gas within the abdominal cavity, such as a stopcock valve 71.

Alternatively, the cannula 70 may comprise the cannula described in the documents referenced above in the description of the trocar 30, or the commercially available cannula used with the commercially available trocars. Additionally, the cannula may comprise the specialty cannula described in U.S. Pat. No. 's 4,943,280, 5,127,909 and 5,129,885. The cannula described in this paragraph are complex with the attendant potential for increased cost. Additionally, such cannula are believed to be difficult to sterilize.

Figure 6:
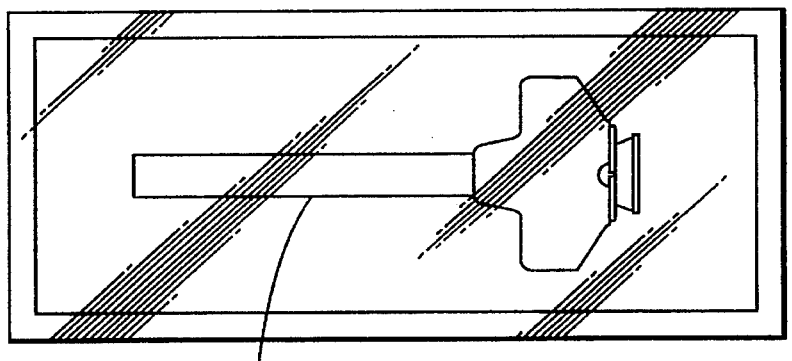

A more cost effective cannula and one which reduces sterilization issues is shown as trocar 60 in FIG. 6. The cannula 60 is free of a means for restricting loss of insufflating gas from the abdominal cavity (e.g. a flapper valve) and is free of a means for affording replenishment of the insufflating gas within the abdominal cavity (e.g. a stopcock).

Figure 8:
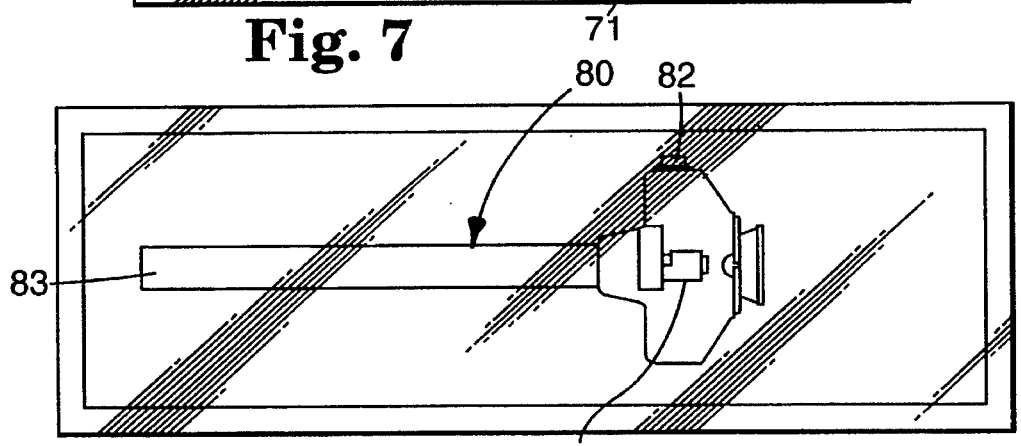

Like the cannula 70, the cannula 80 shown in FIG. 8 comprises a stopcock valve 81 and a valve actuated by button 82. Unlike cannula 70, the cannula 80 has an access tube 83 which is longer (as measured along the elongate axis of the cannula) than the access tube of the cannula 70. The cannula 80 is believed to be particularly useful in specialized procedures, such as a procedure on an obese patient.

Figure 9:
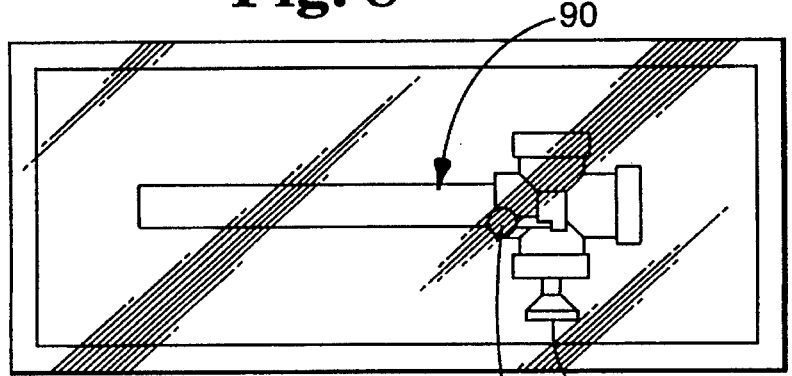

The cannula 90 shown in FIG. 9 is a reusable cannula comprising a stopcock valve 91 and a valve actuated by a button 92. The reusable cannula 90 may be used on a plurality of patients after sterilization, but sterilization is a concern with this type of cannula.

Other examples of different types of cannula include a first cannula that includes predetermined electrical properties, such as a cannula with an electrically insulated access tube, and a second cannula that does not have the predetermined electrical properties. Radiotranslucency is also considered to be a differentiating characteristic that would qualify a radiotranslucent cannula as a different cannula than a non-radiotranslucent cannula according to the present invention. Additionally, specially designed cannulae, customized cannulae and the cannulae described in U.S. Pat. No. 's 4,617,933, 5,002,557, 5,217,451, and 5,122,122 and Published European Patent Application No. 494,520 (the entire contents of each of which are herein expressly incorporated by reference) are also considered to be different types of cannula according to the present invention.

EXAMPLE 1

Referring now to FIG. 1 of the drawing, there is shown an example of a kit assembly 10 according to the present invention.

The kit assembly includes an optional pneumoneedle 100, two disposable cannulae 60, and a cannula 70. The kit assembly also includes a trocar a disposable trocar 20, and a trocar 30 having a means for protecting underlying organs from sharp obturator surfaces.

The kit 10 affords the user the cost savings associated with the trocar 20 and the cannulae 60, yet provides the desirable additional features of the cannula 70 and the trocar 30. Optionally, each of the cannulae 60 and 70, the trocars 20 and 30 and the pneumoneedle 100 may be individually packaged so that, if they are not used during a surgical procedure, they will not be contaminated by the opening of the kit 10.

According to yet another aspect of the present invention, each of the individual trocars and cannulae shown in FIGS. 2 through 9 may be individually packaged. When the trocars and cannulae are individual packaged, surgeons may choose among the various advantages provided by the trocars and obturators according to their preferences.

The present invention has now been described with reference to several embodiments thereof. It will be apparent to those skilled in the art that many changes or additions can be made in the embodiments described without departing from the scope of the present invention. For example, one of either the stopcock 71 or the flapper valve actuated by the button 72 in the cannula 70 may be omitted. Thus, it is the surgeon's preference which dictates which trocars and cannulae are used, as opposed to the dictates of the package system. Thus, the scope of the present invention should not be limited to the structures described in this application, but only by structures described by the language of the claims and the equivalents of those structures.

What is claimed is:

1. A kit assembly for use during a laparoscopic surgery comprising:
    a first trocar for use with a cannula to insert the cannula into the abdominal cavity of a patient, said trocar having a first obturator;
    a second trocar for use with a cannula to insert the cannula into the abdominal cavity of a patient, said second trocar having a second obturator, said first trocar being of a different type of trocar than said second trocar;
    a package for enclosing said first and second trocars,
    wherein said first obturator has sharp cutting surfaces and said first trocar has a means for protecting underlying organs from the sharp obturator surfaces, and
    said second obturator has sharp cutting surfaces and said second trocar is free of a means for protecting underlying organs from the sharp cutting surfaces.

2. A kit assembly according to claim 1 wherein the second trocar comprises a disposable trocar.

3. A kit assembly according to claim 1 wherein said first and second trocar have distal ends, and
    the outer diameter of the first and second trocars at their distal ends are substantially identical.

4. A kit assembly according to claim 1
    wherein one of said first or second trocars comprises a reusable trocar capable of being sterilized and used on different patients.

5. A kit assembly according to claim 1
    wherein one of said first and second trocars comprises a trocar with a disposable obturator.

6. A kit assembly for use during a laparoscopic surgery comprising:
    a first cannula adapted to be inserted into the abdominal cavity of a patient by use of a trocar, said first cannula having an access tube with a lumen having a first inner diameter;
    a second cannula adapted to be inserted into the abdominal cavity of a patient by use of a trocar, said second cannula having an access tube with a lumen having a second inner diameter substantially the same as the first inner diameter;
    a package for enclosing said first and second cannulae wherein said first cannula is of a different type than said second cannula,
    wherein said first cannula has a means for restricting loss of insufflating gas from the abdominal cavity and a means for affording replenishment of the insufflating gas within the abdominal cavity; and
    said second cannula is free of a means for restricting loss of insufflating gas from the abdominal cavity and of a means for affording replenishment of the insufflating gas within the abdominal cavity.

7. A kit assembly according to claim 6 wherein one of said first and second cannulae is disposable.

8. A kit assembly according to claim 6 wherein one of said first and second cannulae is reusable.

9. A kit assembly according to claim 6 wherein the access tube of said first cannula is longer than said access tube of said second cannula.

10. A kit assembly for use during a laparoscopic surgery comprising:
    a first cannula adapted to be inserted into the abdominal cavity of a patient by use of a trocar, said first cannula having an access tube with a lumen having a first inner diameter;
    a second cannula adapted to be inserted into the abdominal cavity of a patient by use of a trocar, said second cannula having an access tube with a lumen having a second inner diameter substantially the same as the first inner diameter;
    a package for enclosing said first and second cannulae wherein said first cannula is of a different type than said second cannula,
    wherein one of said first and second cannulae has predetermined electrical properties and said other of said first and second cannulae is free of said predetermined electrical properties.

* * * * *